United States Patent
Gaston

(10) Patent No.: US 7,931,635 B1
(45) Date of Patent: Apr. 26, 2011

(54) METHOD OF MAKING OVERSIZED ADULT INCONTINENCE DIAPERS EXCEEDING OVERALL WIDTH CAPACITY OF CONVERTING MACHINERY AND DIAPER FORMED THEREBY

(75) Inventor: William W. Gaston, Greenville, NC (US)

(73) Assignee: Attends Healthcare Products, Inc., Greenville, NC (US)

( * ) Notice: Subject to any disclaimer, the term of this patent is extended or adjusted under 35 U.S.C. 154(b) by 194 days.

(21) Appl. No.: 12/321,958

(22) Filed: Jan. 27, 2009

(51) Int. Cl.
*A61F 13/15* (2006.01)
*B29C 65/00* (2006.01)

(52) U.S. Cl. ....... 604/385.201; 604/385.01; 604/385.16; 604/385.22; 156/164

(58) Field of Classification Search ........... 604/385.201, 604/385.01, 385.16, 385.22; 156/164, 519, 156/510
See application file for complete search history.

(56) References Cited

U.S. PATENT DOCUMENTS

| | | | | |
|---|---|---|---|---|
| 3,731,688 | A | * | 5/1973 | Litt et al. ............. 604/365 |
| 4,670,012 | A | | 6/1987 | Johnson ............. 604/390 |
| 4,883,481 | A | | 11/1989 | Blanchard ............. 604/385.1 |
| 5,624,428 | A | * | 4/1997 | Sauer ............. 604/391 |
| 5,846,232 | A | | 12/1998 | Serbiak et al. ............. 604/385.2 |
| 6,494,873 | B2 | | 12/2002 | Karlsson et al. ............. 604/392 |
| 6,648,871 | B2 | | 11/2003 | Kusibojoska et al. ........ 604/392 |
| 2005/0059947 | A1 | | 3/2005 | Murguly ............. 604/387 |
| 2005/0059948 | A1 | | 3/2005 | Murguly ............. 604/387 |
| 2005/0059950 | A1 | | 3/2005 | Murguly ............. 604/387 |
| 2008/0065042 | A1 | | 3/2008 | Wood et al. ............. 604/385.201 |

* cited by examiner

*Primary Examiner* — Jacqueline F Stephens
(74) *Attorney, Agent, or Firm* — K&L Gates LLP

(57) ABSTRACT

Oversized adult diapers are made on converting machinery designed for handling only components no greater than a maximum component width, while utilizing as an outer layer component of the diapers an elongate sheet-like web having a width exceeding the maximum component width of the machinery. The web is pre-formed with at least one folded pleat along a laterally outward margin of the web, such that the pleat reduces the width of the web to less than the maximum component width. The pleat is temporarily tacked to retain the pleat against unfolding while the web is handled by the machinery, but is yieldable to unfold when a diaper made with the web is donned for wearing. The pre-formed pleated web is delivered to the machinery, which is then operated in normal manner to incorporate the web into a plurality of diapers.

9 Claims, 5 Drawing Sheets

METHOD OF MAKING OVERSIZED ADULT INCONTINENCE DIAPERS EXCEEDING OVERALL WIDTH CAPACITY OF CONVERTING MACHINERY AND DIAPER FORMED THEREBY

BACKGROUND OF THE INVENTION

The present invention relates generally to the production of diapers, particularly adult incontinence diapers, and more specifically, to methods of producing such diapers in large sizes.

One of the growing problems in the United States is obesity. In the manufacturer of disposable adult incontinence diapers, this problem has resulted in difficulty in fabricating diapers of a sufficient width to accommodate larger individuals.

Such diapers basically comprise three main components: an inner web or sheet of a liquid permeable material, typically a non-woven, for direct contact with the wearer's body, an intermediate core of a liquid absorbent material typically in the form of a pad of hydrophilic fibers and often including a supplementary absorbent medium such as a super absorbent polymeric material for capturing and holding bodily fluids passing through the permeable inner layer, and an outer web or sheet of a liquid impervious material usually comprised of a laminate of film and non-woven materials to retain liquid within the absorbent core against leakage from the diaper.

In the industry, the sizes of adult incontinence diapers are generally only differentiated in primary sizing groups such as "medium", "large", "extra large" and "extra-extra large". Essentially, while there may be minor differences in the overall length or "rise" of "extra large" and an "extra-extra large" diapers, the only major difference between an "extra large" size diaper and an "extra-extra large" size diaper is in the girth, i.e., the overall outermost width of the diaper which determines the range of wearers' waist sizes the diaper will accommodate, but the widthwise dimension of the central body of the diaper, which comprises the crotch area with the absorbent core, is substantially the same for each diaper.

The so-called "converting" machinery forming the production lines for manufacturing adult diapers necessarily have dimensional limitations and typically are capable of handling sheet feed stock, out of which the inner and outer layers of such diapers are made, only up to a maximum width, e.g., 32 inches, which is insufficient to provide the necessary overall width for a diaper to accommodate an "extra-extra large" waist size. The end result is that incontinent diapers are not available in sufficiently larger sizes to fit many larger individuals. This problem, is only compounded by the fact that a disproportionate number of such individuals have need for incontinent products such as diapers.

While the above-described problem can be overcome by constructing converting machinery in larger dimensions to accommodate wider sheet feed stock materials, a single converting line of equipment typically costs many millions of dollars to construct, which necessarily makes this solution extremely expensive and highly impractical. Hence, a need exists in the industry for a way to efficiently mass produce adult incontinence diapers in "extra-extra large" sizes, utilizing existing converting machinery without requiring modification thereof.

SUMMARY OF THE INVENTION

It is accordingly an object of the present invention to provide a method for producing adult incontinence diapers which overcomes the problems discussed above. A more specific object of the invention is to provide such a method by which "extra-extra large" sizes of such diapers may be produced utilizing existing unmodified converting machinery.

Briefly summarized, the present invention provides a method of making oversized adult incontinence diapers on converting machinery having a maximum widthwise capacity for handling only components equal to or less that a corresponding maximum component width, while utilizing as an outer layer component of the diapers, among other possible components, an elongate sheet-like open-width web of indeterminate continuous length having a fully-open widthwise dimension which exceeds the maximum component width of the machinery.

According to the present method, the web is pre-formed with at least one folded pleat extending along a laterally outward margin of the web, such that the at least one pleat reduces the widthwise dimension of the web to less than the maximum component width. The folding of the web at the pleat is temporarily tacked sufficiently to retain the pleat against unfolding while the web is handled by the machinery, but is yieldable to unfold the web into fully-open width in response to exertion of an unfolding force against the pleat when a diaper made with the web is donned for wearing. Thus, the pre-formed pleated web is delivered to the machinery, which is then operated in normal manner to incorporate the web into a plurality of diapers.

In a preferred embodiment of the present method, a pair of the folded pleats are formed to extend respectively along opposed laterally outward margins of the web laterally outwardly of a central longitudinal region which resides adjacent a liquid containment area of the diapers. The folded pleats are preferably formed continuously along the entire longitudinal extent of the web. Tacking of the folded pleats may be accomplished in any know manner, such as by ultrasonically tack-welding the overlapping folds of the pleats together.

The method of the present invention requires no modification of the structure or the normal operation of the converting machinery to form the web into diapers. For example, the machinery may periodically sever sections from opposed laterally outward margins of the web in a known manner to form each diaper of an hourglass shape with laterally outwardly projecting tab sections which include the folded pleats. Likewise, the machinery may also execute the usual known manner of placing an absorbent core at the central longitudinal region of the web in each diaper.

According to another aspect of the present invention, a novel diaper is made according to the method of the invention. More specifically, a diaper according to the present invention comprises an outer layer of a sheet-like web in an hourglass shape defining front and back panels each having outwardly-extending tab sections at opposite lateral sides and a constricted central crotch area therebetween. At least two of the tab sections include a folded pleat in the web generally parallel to the laterally outward sides of the tab sections, and the pleats are temporarily tacked to retain the pleats against unintended unfolding but the tacking is yieldable to unfold the pleats in response to exertion of an unfolding force against the pleats when the diaper is donned for wearing.

Advantageously, the methodology of the present invention enables converting machinery, without machine modification, to fabricate oversized diapers from oversized sheet roll stock. For example, a machine line whose maximum widthwise capacity is to accommodate incoming open-width sheet feed stock not greater than 32 inches in width may, by appropriate pleating and tacking of the sheet feed stock, accommodate feed stock of a 36 inch width or even wider.

DETAILED DESCRIPTION OF THE PREFERRED EMBODIMENTS

Figure 1:
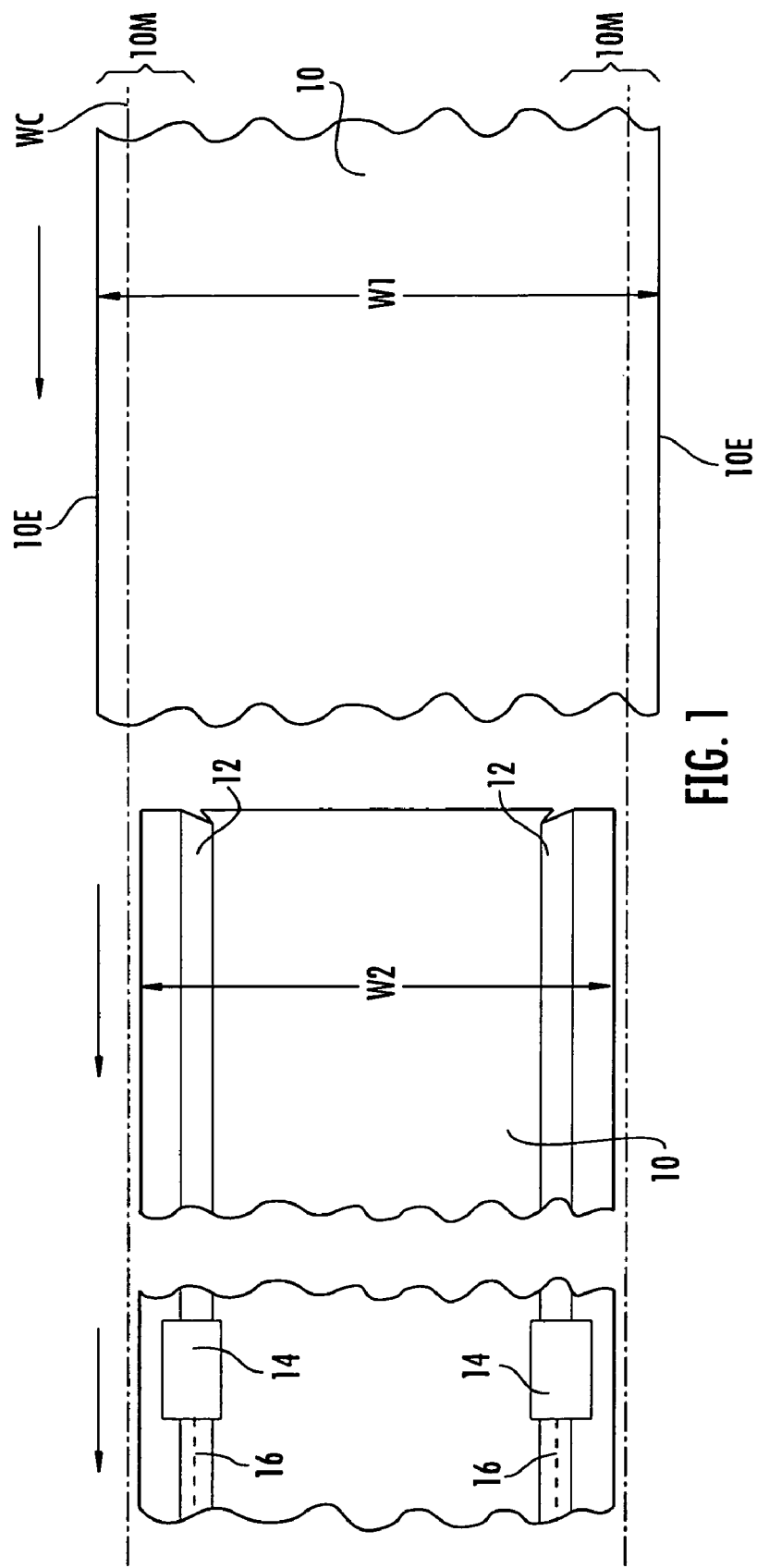
FIG. 1 is a schematic depiction in top plan view showing the sequential steps of a web to be used as an outer layer component of diapers being pre-formed with folded pleats extending along laterally outward margins of the web followed by temporary tacking of the pleats, in accordance with a preferred embodiment of the method of the present invention.
Figure 2:
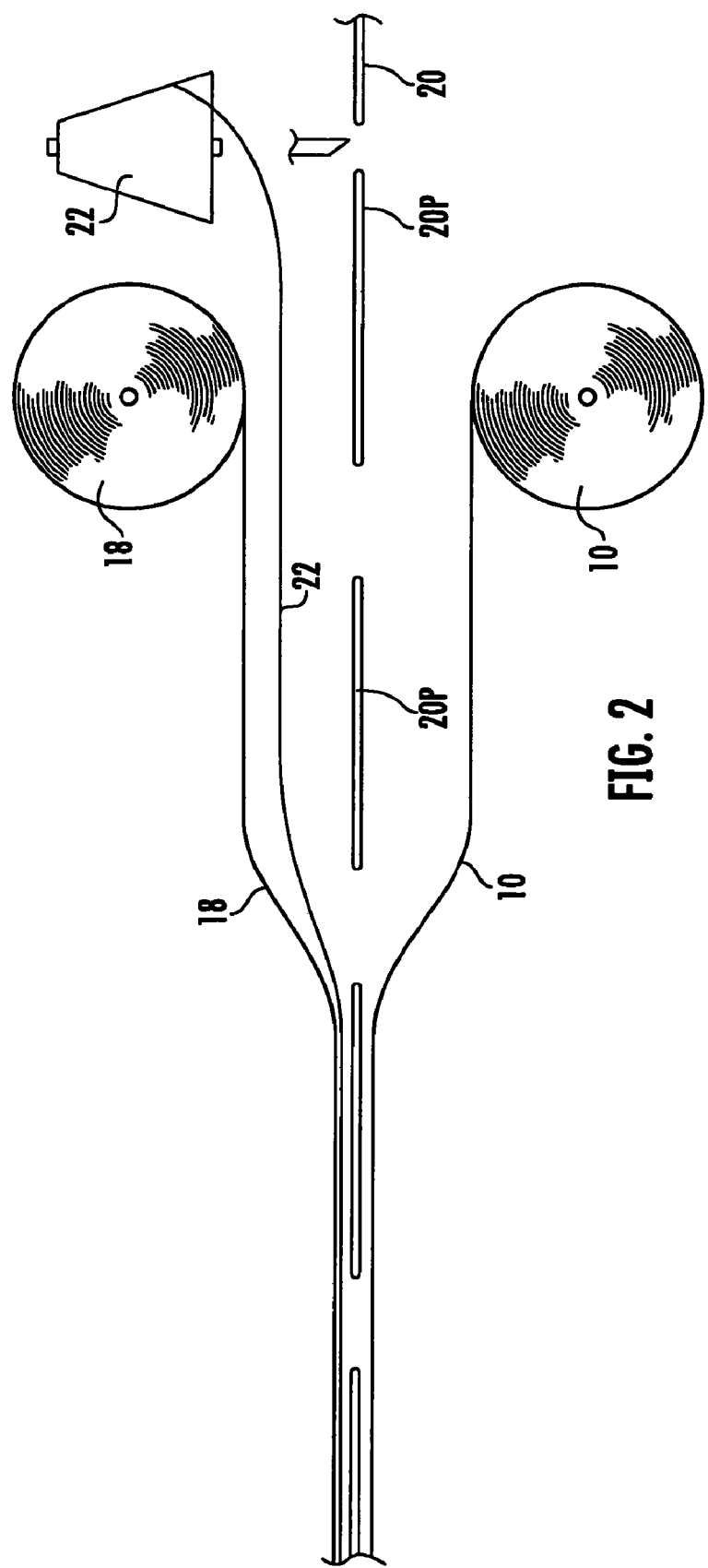
FIG. 2 is a schematic depiction in side elevation showing the initial steps of assembly of the pre-formed web of FIG. 1 with other components into a composite diaper structure to begin the formation of a plurality of diapers, in accordance with a preferred embodiment of the method of the present invention.
Figure 3:
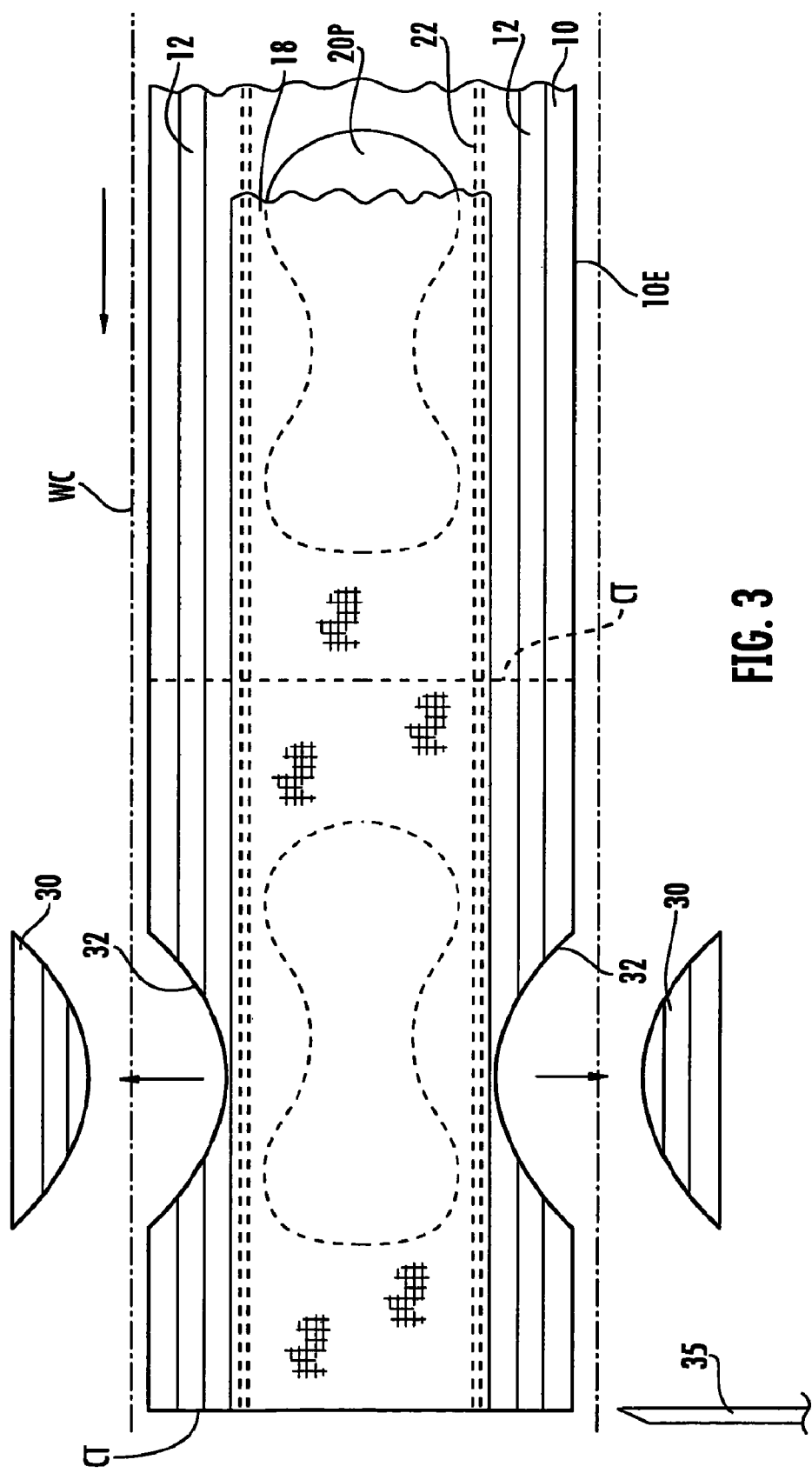
FIG. 3 is a schematic depiction in top plan view of the sequential steps, following the steps of FIG. 2, in severing of sections from opposed laterally outward margins of the composite diaper structure to form each diaper of an hourglass shape, followed by the transverse cutting of the composite diaper structure to produce plural discrete diapers, also according to a preferred embodiment of the method of the present invention.

Referring now to the accompanying drawings, and initially to FIGS. 1-3, the basic sequence of steps in the methodology contemplated by the present invention are shown in sequence progressing from FIG. 1 to FIG. 2 to FIG. 3. Fundamentally, as previously noted, the present invention contemplates the formation of adult incontinence diapers in "extra-extra large" sizes by the specialized pre-formation of a web to be utilized as the liquid impervious outer web in an otherwise conventional composite diaper construction so as to impart lateral expandability to such web, whereby the conventional methodology and conventional machinery utilized in the current state of the art for mechanized automated manufacture of such diapers need not be altered or modified in order to produce diapers in such sizes. Hence, in the accompanying drawings as well as in the following specification of the present invention, the diaper fabricating methodology and converting machinery as already known among persons of ordinary skill in the relevant industry are depicted only schematically and only to the extent reasonably necessary to facilitate an understanding of the improvements provided by the present invention.

FIG. 1 depicts at 10 a typical sheet-like web of a liquid impervious material such as a laminate of thermoplastic film and non-woven material commonly used in diaper construction to serve as the outer layer, also sometimes called the bottom layer, of the composite body of a diaper. The web 10 as conventionally utilized is of a flat open-width sheet-like configuration having substantially parallel linear longitudinal edges 10E along opposite outer lateral sides and typically wound for storage about a core in a roll-type form. As described previously, the web 10 would conventionally have a lateral width not greater than the maximum widthwise capacity of the conventional so-called "converting" machinery used in industry for manufacturing adult diapers.

However, according to the present invention, the web 10 has a lateral width dimension W1 in full open-width form which is a predetermined selected dimension greater than the lateral widthwise capacity of the converting machinery on which the web 10 will be processed and assembled with, other components into a diaper structure. In FIG. 1, and also in FIG. 3, the maximum widthwise capacity of such converting machinery is represented at WC for reference purposes. According to the present invention, the web 10 is processed through a preliminary step as depicted in FIG. 1 to form at least one folded pleat 12, but preferably two folded pleats 12, extending the full length of the web 10 along each laterally outward margin 10M of the web 10 at a slight laterally inward spacing from the outermost side edges 10E of the web 10, thereby to reduce the overall widthwise dimension of the web 10 to a dimension W2 which corresponds to or is less than the maximum widthwise capacity WC of the converting machinery. For example, typical conventional converting machines are capable of handling sheet feed stock of only up to a maximum width of 32 inches. By pre-forming the web 10 with the two folded pleats 12, a web 10 of a 36 inch width W1 may be conveniently reduced to an overall width W2 of 32 inches or slightly less than 32 inches (e.g., 31.5 inches) so as to be capable of being handled by the converting machinery.

To retain the pleats against undesired unintended unfolding, the pleats 12 are temporarily tacked to adhere or fuse the overlapping folded layers of the web 10 at the pleats 12 with sufficient adhesive or cohesive strength to retain the pleats against the forces exerted on the web 10 during handling by the converting machinery, but the tacks are of sufficiently limited strength to yield readily to a manual force exerted in the opposite laterally outward directions relative to the widthwise extent of the web without tearing or damaging the web such that the pleats 12 may be unfolded when desired, e.g., when a diaper made with the web is later being donned for wearing by a user.

Such tacking of the pleats 12 may be accomplished in various known ways which will be readily recognized by persons of ordinary skill in the art. The presently contemplated and preferred manner of tacking the pleats 12 is by periodic ultrasonic welding of the overlapping folds of the pleats 12 via known ultrasonic welding devices, shown only schematically at 14 in FIG. 1, which serve to lightly fuse the contacting surfaces of the overlapping folds forming a series of low-strength point-like tack welds represented schematically at 16 in FIG. 1. Following the pre-formation of the web 10 with the tack-welded pleats 12, the web 10 is wound into roll-form for storage and subsequent processing into diapers.

With reference to FIG. 2, the typical manner of fabrication of the web 10 together with other diaper components is depicted in a highly schematic and simplified form. Most basically, a conventional adult incontinence diaper comprises a liquid impervious outer layer such as the web 10, together with a liquid pervious or permeable inner layer, commonly in the form of a non-woven web 18 also of a flat open-width sheet-like configuration like the web 10, and a liquid absorbent core material 20 disposed between the webs 10, 18. For example, the absorbent core material 20 may be a non-woven web of absorbent padding comprised of hydrophilic fibers which may also incorporate supplementary absorbent media such as a super absorbent polymeric material impregnated in, intermingled with, or otherwise contained by the absorbent web. Other common components of disposable diapers are also preferably incorporated into the diaper structure, such as elastic filaments 22.

Those persons skilled in the art will recognize and understand that other possible components of disposable diapers not shown in the drawings may also be utilized and incorporated into the diaper structure, e.g., a perforated acquisition distribution film layer. These and other common diaper construction elements are not excluded from use in the present invention but do not form a part of the novelty of the present invention and are not believed to be necessary to facilitate an enabling understanding of the invention or its preferred embodiment.

Each of the outer and inner webs 10, 18 are stored on and fed from respective storage rolls 24, 26 on which an elongate continuous indeterminate length of each web is wound; with the webs being fed therefrom to advance in essentially flat open-width form in a common direction for assembly together in widthwise and lengthwise facing relation to one another, as depicted in FIG. 2. As the outer and inner webs 10, 18 are thusly advanced, the web of absorbent core material 20 is correspondingly advanced from a suitable source of supply to be fed between the outer and inner webs 10, 18, for assembly therewith as an intermediate absorbent layer.

The absorbent web 20 is preferably cut as it is advanced into discrete absorbent pads 20P which are delivered between the outer and inner webs 10, 18 at lengthwise spacings from one another to form respective absorbent crotch pads in discrete diapers to be subsequently formed in the known conventional manner. As this technique is commonly used in the industry, the cutting and delivery of the absorbent pads 20P is only schematically depicted in FIG. 2 by the discrete absorbent pads 20P advancing forwardly from a cutting element represented only by knife 28. In the cutting of the absorbent web 20 into the discrete absorbent pads 20P, it is additionally preferred that each pad 20P be cut into an oblong hour glass configuration, as best seen in FIG. 3, in conformity to the general shape of the crotch and adjacent forward and rearward areas in a diaper when worn.

Simultaneously, the elastic filaments 22 are also fed between the outer and inner webs 10, 18 to also be assembled therewith. These respective components are joined together in any suitable known manner, such as the ultrasonic welding of the respective webs 10, 18 together, thereby capturing and retaining the absorbent pads 20 and the elastic filaments 22 in assembly with and between the outer and inner webs 10, 18 into a unified composite diaper structure, all in conventional manner.

FIG. 3 depicts in top plan view the advancement through the converting machinery of the composite diaper structure produced by the above-described steps shown in FIG. 2. As the basic structure and operation of such converting machinery is known in the industry, the machinery is not depicted in FIG. 3 other than the representation at WC of the maximum widthwise capacity of the machinery. As will be seen, the inner web 18 is preferably of a narrower widthwise dimension than that of the outer web 10 and is situated centrally along the length of the outer web 10 overlying the absorbent pads 20P and the elastic filaments 22 disposed on opposite sides of the absorbent pads 20 adjacent the laterally outermost edges of the inner web 18. As will be seen, the tack-welded pleats 12 in the outer web 10 are situated laterally outwardly of the outermost edges of the inner web 18.

As the composite diaper structure continues to advance downstream along the production line of the converting equipment, additional cutting implements (not shown) are activated to sever from each opposite side of the outer web 10 symmetrical, generally arcuate segments 30 adjacent each absorbent pad 20P outwardly of each lateral side of the inner web 18, thereby forming the composite diaper structure into a series of repeating hourglass shapes each representing an individual diaper structure. Subsequently, the composite diaper structure is cut transversely across the entire width thereof via any suitable cutting implement, e.g., a knife 35, at locations intermediately between the absorbent pads 20P and the outwardly adjacent arcuate cutouts 32, as represented by cutting line CT in FIG. 3. In this manner, the composite diaper structure is severed repeatedly at each transverse cutting line CT thereby progressively producing an accumulating plurality of identical discrete diapers, as represented by the diaper 34 in FIG. 4.

Figure 4:
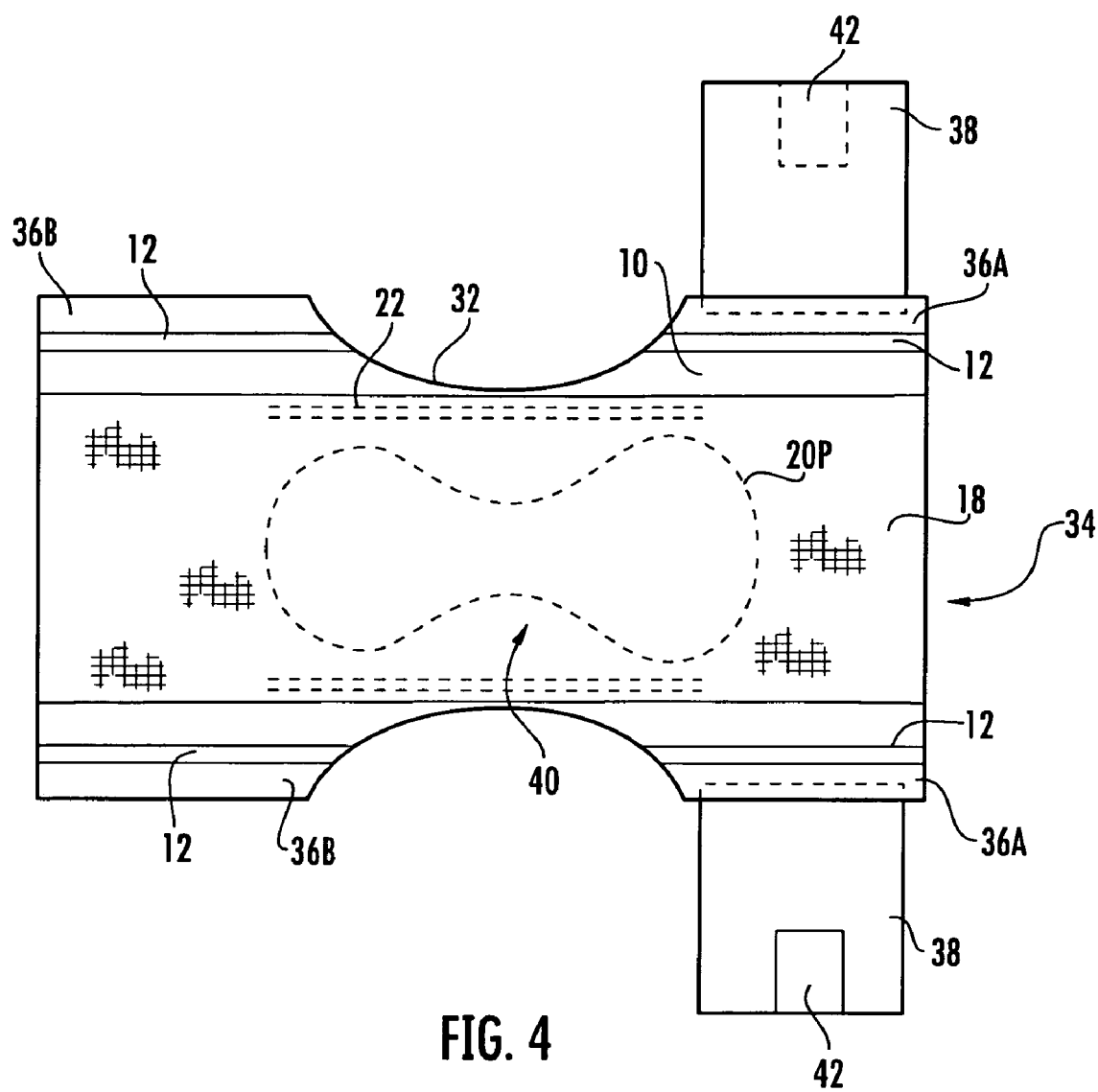
FIG. 4 is a schematic top plan view of a diaper made in accordance with a preferred embodiment of the method of the present invention depicted in FIGS. 1-3.

FIG. 4 depicts schematically the basic construction of each resulting diaper 34. For sake of clarity, the diaper 34 in FIG. 4 is depicted with the elastic filaments 22 still stretched in an elongated state representative of the condition in which the filaments are held throughout the method steps depicted from FIG. 2 through the severing of the discrete individual diapers in FIG. 3. However, those persons skilled in the art will recognize that, upon the severing of the individual diapers 34, the elastic filaments 22 will be allowed to relax longitudinally and thereby to constrict the adjacent edges of the arcuate cutouts 32.

Each diaper 34 is thusly formed of an overall hourglass configuration with the main central longitudinal section of the diaper forming a main central diaper body 40 comprising basically an outer layer of the web 10, an inner layer of the web 18, and a single absorbent pad 20 disposed therebetween to form a central liquid containment area of the diaper 34, and with four wing-like tab sections 36A, 36B of the outer web 10 projecting laterally outwardly from the main diaper body 40 at each opposite lateral side and each opposite end thereof.

Tab extensions 38 are preferably affixed, e.g., adhesively or via ultrasonic welding or any other suitable means of affixation, to opposite lateral side edges of the tab sections 36A of the outer web 10 adjacent one severed end thereof and laterally outwardly of the tack-welded pleats 12, thereby to increase the waist-encircling girth of the overall diaper 34. Each tab extension 38 preferably includes an adhesive section 42. The tab extensions 38 may be affixed to the outer web 10 either prior or subsequent to the severing of the composite diaper structure into discrete diapers 34.

As will be understood, the diaper 34 may be conveniently worn by positioning the main diaper body 40 between the legs of a wearer with the arcuate cutouts 32 positioned in the wearer's crotch area, with the tab sections 36A having the tabs extensions 38 situated to the rear of the wearer and the tab sections 36B situated forwardly of the wearer. With the forward end of the diaper 34 held against the wearer's lower abdomen, the opposing tab extensions 38 of the tab sections 36A may be brought forwardly at each side of the wearer's body to encircle the wearer's waist and overlap the respective forwardly positioned tab sections 36B whereby the adhesive sections 42 of the tab extensions 38 may be secured to the tab sections 36B to retain the diaper in place. The elastic filaments along the arcuate cutouts 32 assist in conforming the cutouts 32 to the upper legs of the wearer at the crotch area to provide a comfortable and secure fit.

Figure 5:
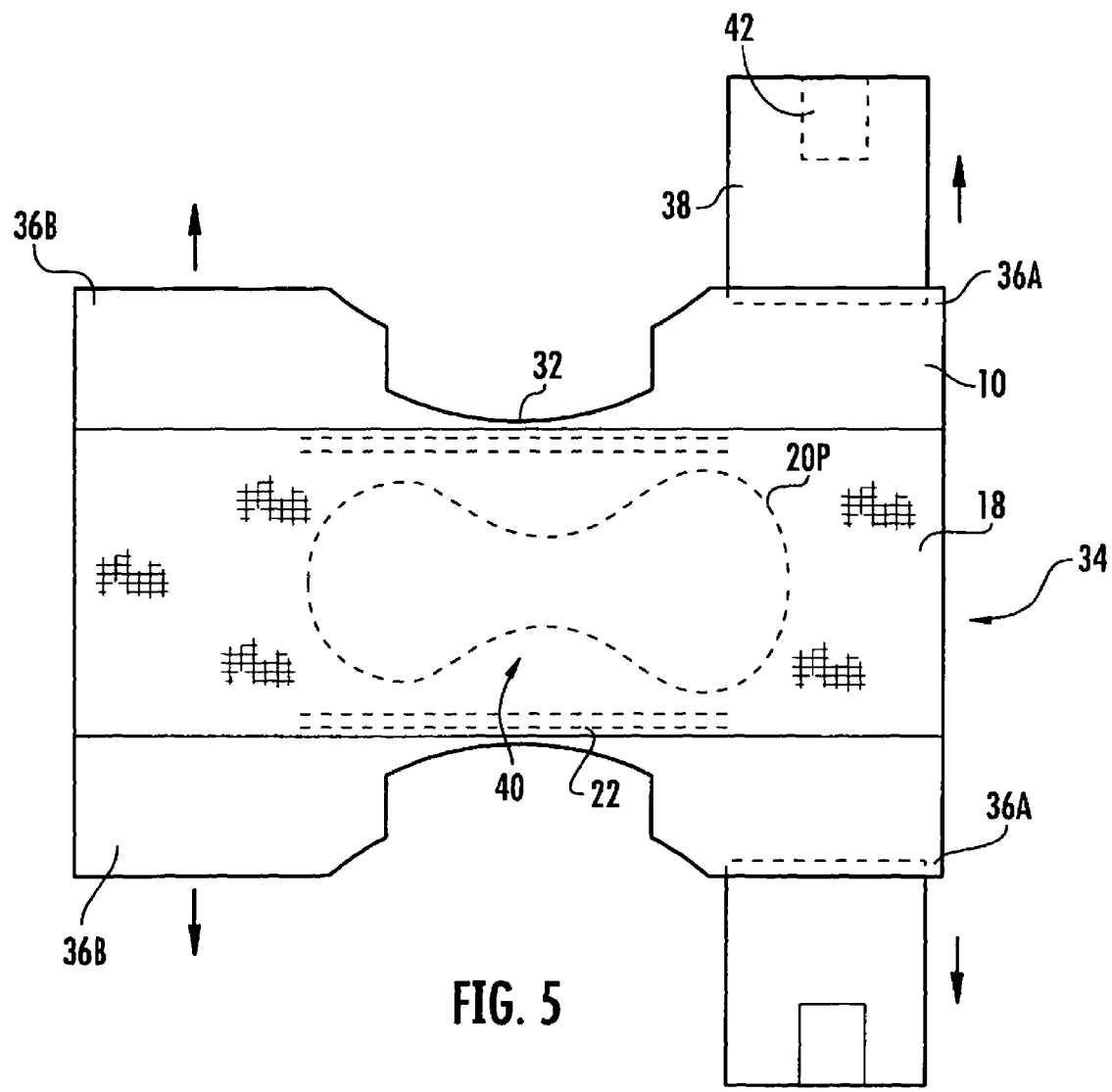
FIG. 5 is another schematic top plan view of the diaper of FIG. 4, depicting the unfolding of the tacked pleats for use of the diaper, according to the present invention.

As will be understood, in the described process of donning the diaper 34 for wearing, the wearer can conveniently exert a manual force on any one or more or all of the tab sections 36A, 36B as the tab sections are brought into overlapping relation to break the tack welds holding the pleats 12, thereby allowing the pleats 12 to unfold and provide an increased girth to the diaper 34 as necessary to fit a wearer with a large waist, all as representatively depicted in FIG. 5. Thus, by the use of the tack-welded pleats 12, a diaper 34 may be produced of a size comparable to that of a typical "extra large" range of waist sizes, but through the extendibility of the pleats 12, to provide the greater girth necessary to fit "extra-extra large"

individuals, all without requiring any modification of the converting machinery used to produce the diapers.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of making oversized adult incontinence diapers, comprising the steps of:
   (a) providing machinery forming a manufacturing line for assembling components into diapers, wherein the machinery has a maximum widthwise capacity for handling components equal to or less that a corresponding maximum component width;
   (b) providing an elongate sheet-like open-width web of indeterminate continuous length for use as an outer layer component of diapers, wherein the web has a fully-open widthwise dimension which exceeds the maximum component width;
   (c) pre-forming the web with at least one folded pleat extending along a laterally outward margin of the web, the at least one pleat reducing the widthwise dimension of the web to equal to or less than the maximum component width;
   (d) temporarily tacking the web sufficiently to retain the pleat against unfolding while the web is handled by the machinery but yieldable to release the tacking to unfold the web without damage thereto into fully-open width in response to exertion of an unfolding force against the pleat when a diaper made with the web is donned for wearing;
   (e) delivering the pre-formed pleated web to the machinery, and
   (f) operating the machinery to incorporate the web into a plurality of diapers.

2. A method of making oversized adult incontinence diapers according to claim 1, wherein the pre-forming of the web comprises forming a pair of folded pleats respectively extending along opposed laterally outward margins of the web.

3. A method of making oversized adult incontinence diapers according to claim 1, wherein the web includes a central longitudinal region to reside adjacent a liquid containment area of the diapers, and the pre-forming of the web comprises locating the at least one folded pleat laterally outwardly of the central longitudinal region.

4. A method of making oversized adult incontinence diapers according to claim 1, wherein the at least one folded pleat is formed continuously along the entire longitudinal extent of the web.

5. A method of making oversized adult incontinence diapers according to claim 1, wherein the step of operating the machinery to incorporate the web into diapers includes periodically severing sections from opposed laterally outward margins of the web to form each diaper of an hourglass shape with laterally outwardly projecting tab sections which include the at least one folded pleat.

6. A method of making oversized adult incontinence diapers according to claim 1, wherein the step of operating the machinery to incorporate the web into diapers includes placing an absorbent core at the central longitudinal region of the web in each diaper.

7. A method of making oversized adult incontinence diapers according to claim 1, wherein the tacking of the at least one folded pleat comprises ultrasonically tack-welding overlapping folds of the at least one pleat together.

8. A diaper made according to the method of claim 1.

9. A diaper comprising an outer layer of a sheet-like web in an hourglass shape defining front and back panels each having unitary outwardly-extending tab sections at opposite lateral sides and a constricted central crotch area therebetween, at least two of the tab sections including a folded pleat in the web generally parallel to the laterally outward sides of the tab sections, the pleats being temporarily tacked to retain the pleats against unintended unfolding but yieldable to release the tacking to unfold without damage to the tab sections in response to exertion of an unfolding force against the pleats when the diaper is donned for wearing, two of the tab sections supporting an adhesive section laterally outwardly of the pleat for securing the tab sections of the front and back panels together when the diaper is worn.

\* \* \* \* \*